United States Patent [19]

Takiguchi et al.

[11] Patent Number: 4,968,614
[45] Date of Patent: Nov. 6, 1990

[54] HUMAN PANCREATIC ELASTASE I

[75] Inventors: Yo Takiguchi; Tokio Tani; Hidehiko Furukawa; Ohmine, Toshinori; Kawashima, Ichiro, all of Hiromachi, Japan

[73] Assignee: Sankyo Company Limited, Tokyo, Japan

[21] Appl. No.: 40,631

[22] Filed: Apr. 21, 1987

[30] Foreign Application Priority Data

Apr. 26, 1986 [JP] Japan ................................. 61-97259

[51] Int. Cl.⁵ ...................... C12N 15/00; C12P 21/06; C12P 21/02; C12P 21/04
[52] U.S. Cl. .............................. 435/172.3; 435/70.3; 435/71.2; 435/91; 435/218; 435/252.31; 435/252.33.320; 536/27; 530/350; 935/18; 935/29; 935/32; 935/34; 935/48; 935/56; 935/58; 935/61; 935/70; 935/73; 935/74; 935/82
[58] Field of Search ...................... 435/68, 70, 218, 49, 435/70.3, 71.2, 252.31, 252.33, 320; 536/27; 924/94; 935/14

[56] References Cited

U.S. PATENT DOCUMENTS 4,666,847 5/1987 Alford et al. ...................... 435/253

FOREIGN PATENT DOCUMENTS 0157604 10/1985 European Pat. Off. ........... 435/69.1

OTHER PUBLICATIONS

Takasugi, S. et al., Chemical Abstracts, vol. 96, p. 274, Abstract No. 30803P (1982).
Nakao, J. et al., Chemical Abstracts, vol. 88, p. 156, Abstract No. 84994e (1977).
Biochemistry 1987, 26, pp. 3447–3452, Primary Structure of Human Pancreatic Protease E Determined by Sequence Analysis of the Cloned mRNA, Shen et al.
Takahashi et al, Biochem. J. (1985) 231, pp. 229–232, "A New Site–Specific Endonuclease, ScaI, from *Streptomyces casepitosus*".
Largman et al., Biochem. 15, pp. 2491–2500 (1976), "Purification and Characterization of Two Human Pancreatic Elastases".
Largman et al., Biochem. Biophys. Act, 6233, pp. 208–212 (1980), Human Pancreatic Proelastase 2 Sequence of the Activation Peptide.

*Primary Examiner*—Robin L. Teskin
*Assistant Examiner*—Joan Ellis
*Attorney, Agent, or Firm*—Frishauf, Holtz, Goodman & Woodward

[57] ABSTRACT

Human pancreatic elastase I can be obtained by genetic engineering.

2 Claims, 13 Drawing Sheets

```
(N)-Val Val Gly Gly Thr Glu Ala Gly Arg Asn Ser Trp
Pro Ser Gln Ile Ser Leu Gln Tyr Arg Ser Gly Gly Ser
Trp Tyr His Thr Cys Gly Gly Thr Leu Ile Arg Gln Asn
Trp Val Met Thr Ala Ala His Cys Val Asp Tyr Gln Lys
Thr Phe Arg Val Val Ala Gly Asp His Asn Leu Ser Gln
Asn Asp Gly Thr Glu Gln Tyr Val Ser Val Gln Lys Ile
Val Val His Pro Tyr Trp Asn Ser Asp Asn Val Ala Ala
Gly Tyr Asp Ile Ala Leu Leu Arg Leu Ala Gln Ser Val
Thr Leu Asn Ser Tyr Val Gln Leu Gly Val Leu Pro Gln
Glu Gly Ala Ile Leu Ala Asn Asn Ser Pro Cys Tyr Ile
Thr Gly Trp Gly Lys Thr Lys Thr Asn Gly Gln Leu Ala
Gln Thr Leu Gln Gln Ala Tyr Leu Pro Ser Val Asp Tyr
Ala Ile Cys Ser Ser Ser Ser Tyr Trp Gly Ser Thr Val
Lys Asn Thr Met Val Cys Ala Gly Gly Asp Gly Val Arg
Ser Gly Cys Gln Gly Asp Ser Gly Gly Pro Leu His Cys
Leu Val Asn Gly Lys Tyr Ser Leu His Gly Val Thr Ser
Phe Val Ser Ser Arg Gly Cys Asn Val Ser Arg Lys Pro
Thr Val Phe Thr Arg Val Ser Ala Tyr Ile Ser Trp Ile
Asn Asn Val Ile Ala Ser Asn -(C).
```

(N)-Val Val Gly Gly Thr Glu Ala Gly Arg Asn Ser Trp
Pro Ser Gln Ile Ser Leu Gln Tyr Arg Ser Gly Gly Ser
Trp Tyr His Thr Cys Gly Gly Thr Leu Ile Arg Gln Asn
Trp Val Met Thr Ala Ala His Cys Val Asp Tyr Gln Lys
Thr Phe Arg Val Val Ala Gly Asp His Asn Leu Ser Gln
Asn Asp Gly Thr Glu Gln Tyr Val Ser Val Gln Lys Ile
Val Val His Pro Tyr Trp Asn Ser Asp Asn Val Ala Ala
Gly Tyr Asp Ile Ala Leu Leu Arg Leu Ala Gln Ser Val
Thr Leu Asn Ser Tyr Val Gln Leu Gly Val Leu Pro Gln
Glu Gly Ala Ile Leu Ala Asn Asn Ser Pro Cys Tyr Ile
Thr Gly Trp Gly Lys Thr Lys Thr Asn Gly Gln Leu Ala
Gln Thr Leu Gln Gln Ala Tyr Leu Pro Ser Val Asp Tyr
Ala Ile Cys Ser Ser Ser Ser Tyr Trp Gly Ser Thr Val
Lys Asn Thr Met Val Cys Ala Gly Gly Asp Gly Val Arg
Ser Gly Cys Gln Gly Asp Ser Gly Gly Pro Leu His Cys
Leu Val Asn Gly Lys Tyr Ser Leu His Gly Val Thr Ser
Phe Val Ser Ser Arg Gly Cys Asn Val Ser Arg Lys Pro
Thr Val Phe Thr Arg Val Ser Ala Tyr Ile Ser Trp Ile
Asn Asn Val Ile Ala Ser Asn -(C).

FIG. 6

(5')-GTA GTC GGA GGG ACT GAG GCC GGG AGG AAT TCC TGG
CCC TCT CAG ATT TCC CTC CAG TAC CGG TCT GGA GGT TCC
TGG TAT CAC ACC TGT GGA GGG ACC CTT ATC AGA CAG AAC
TGG GTG ATG ACA GCT GCT CAC TGC GTG GAT TAC CAG AAG
ACT TTC CGC GTG GTG GCT GGA GAC CAT AAC CTG AGC CAG
AAT GAT GGC ACT GAG CAG TAC GTG AGT GTG CAG AAG ATC
GTG GTG CAT CCA TAC TGG AAC AGC GAT AAC GTG GCT GCC
GGC TAT GAC ATC GCC CTG CTG CGC CTG GCC CAG AGC GTT
ACC CTC AAT AGC TAT GTC CAG CTG GGT GTT CTG CCC CAG
GAG GGA GCC ATC CTG GCT AAC AAC AGT CCC TGC TAC ATC
ACA GGC TGG GGC AAG ACC AAG ACC AAT GGG CAG CTG GCC
CAG ACC CTG CAG CAG GCT TAC CTG CCC TCT GTG GAC TAT
GCC ATC TGC TCC AGC TCC TCC TAC TGG GGC TCC ACT GTG
AAG AAC ACC ATG GTG TGT GCT GGT GGA GAT GGA GTT CGC
TCT GGA TGT CAG GGT GAC TCT GGG GGC CCC TCA TGC
TTG GTG AAT GGC AAG TAT TCT CTC CAT GGA GTG ACC AGC
TTT GTG TCC AGC CGG GGC TGT AAT GTC TCC AGG AAG CCT
ACA GTC TTC ACC CGG GTC TCT GCT TAC ATC TCC TGG ATA
AAT AAT GTC ATC GCC TCC AAC X -(3')

FIG.7

```
         10        20        30    /   40        50         6,0
AGCTTAGTACTCAGGACCTTCCGGAAACCAATGCCCGGGTAGTCGGAGGGACTGAGGCCG
    ATCATGAGTCCTGGAAGGCCTTTGGTTACGGGCCCATCAGCCTCCCTGACTCCGGC
                                         2
         70        80        90   3  100       110         120
GGAGGAATTCCTGGCCCTCTCAGATTTCCCTCCAGTACCGGTCTGGAGGTTCCTGGTATC
CCTCCTTAAGGACCGGGAGAGTCTAAAGGGAGGTCATGGCCAGACCTCCAAGGACCATAG
                                4
        130  5   140       150       160       170,        180
ACACCTGTGGAGGGACCCTTATCAGACAGAACTGGGTGATGACAGCTGCACACTGCGTGG
TGTGGACACCTCCCTGGGAATAGTCTGTCTTGACCCACTACTGTCGACGTGTGACGCACC
                           6

190  7  200        210       220       230         240
ATTACCAGAAGACTTTCCGCGTGGTGGCTGGAGACCATAACCTGAGCCAGAATGATGGCA
TAATGGTCTTCTGAAAGGCGCACCACCGACCTCTGGTATTGGACTCGGTCTTACTACCGT
                        8
      9   250       260        270       280        290   //  300
CTGAGCAGTACGTGAGTGTGCAGAAGATCGTGGTGCATCCATACTGGAACAGCGATAACG
GACTCGTCATGCACTCACACGTCTTCTAGCACCACGTAGGTATGACCTTGTCGCTATTGC
 10                                                         12
        310       320       330   13  340       350,        360
TGGCTGCAGGCTATGACATCGCCCTGCTGCGCCTGGCCCAGAGCGTTACCCTCAATAGCT
ACCGACGTCCGATACTGTAGCGGGACGACGCGGACCGGGTCTCGCAATGGGAGTTATCGA
                                 14
         370 15  380        390        400       410   /7  420
 ATGTCCAGCTGGGTGTTCTGCCCCAGGAGGGAGCCATCCTGGCTAACAACAGTCCCTGCT
TACAGGTCGACCCACAAGACGGGGTCCTCCCTCGGTAGGACCGATTGTTGTCAGGGACGA
            16                                       18
        430       440       450       460   19  470          480
ACATCACAGGCTGGGGCAAGACCAAGACCAATGGGCAGCTGGCCCAGACCTTGCAGCAGG
TGTAGTGTCCGACCCCGTTCTGGTTCTGGTTACCCGTCGACCGGGTCTGGAACGTCGTCC
                                                     20
         490       500  2/ 510       520         ,530         540
CTTACCTGCCCTCTGTGGACTATGCCATCTGCTCCAGCTCCTCCTACTGGGGCTCCACTG
GAATGGACGGGAGACACCTGATACGGTAGACGAGGTCGAGGAGGATGACCCCGAGGTGAC
                                 22
   23  550       560       570       580       590          600
TGAAGAACACCATGGTGTGTGCTGGTGGAGATGGAGTTCGCTCTGGATGTCAGGGTGACT
ACTTCTTGTGGTACCACACACGACCACCTCTACCTCAAGCGAGACCTACAGTCCCACTGA
 24
    25  610       620       630       640       650         660
CTGGGGGCCCCCTCCATTGCTTGGTGAATGGCAAGTATTCTCTCCATGGAGTGACCAGCT
GACCCCCGGGGGAGGTAACGAACCACTTACCGTTCATAAGAGAGGTACCTCACTGGTCGA
 26
   27  670       680        ,690       700       710   29  720
TTGTGTCCAGCCGGGGCTGTAATGTCTCTAGAAAGCCTACAGTCTTCACACGGGTCTCTG
AACACAGGTCGGCCCCGACATTACAGAGATCTTTCGGATGTCAGAAGTGTGCCCAGAGAC
 28                                                         30
        ,730       740       750  3/  760       770
CTTACATCTCCTGGATAAATAATGTCATCGCCTCCAACTGAAGATCTG
GAATGTAGAGGACCTATTTATTACAGTAGCGGAGGTTGACTTCTAGACCTAG
                                              32
```

FIG.8

```
                                                    -10
... tcttctgccccacaaag GA GAC AGC ACC CAG GAC
                                  His Ser Thr Gln Asp Exon 2           1
CTT CCG GAA ACC AAT GCC CGC GTA GTC GGA GGG
Leu Pro Glu Thr Asn Ala Arg Val Val Gly Gly 10
ACT GAG GCC GGG AGG AAT TCC TGG CCC TCT CAG
Thr Glu Ala Gly Arg Asn Ser Trp Pro Ser Gln
gtgggtctccttccc ....      ...... tttcctccccat 20         Exon 3
ctag ATT TCC CTC CAG TAC CGG TCT GGA GGT TCC
     Ile Ser Leu Gln Tyr Arg Ser Gly Gly Ser 30
TGG TAT CAC ACC TGT GGA GGG ACC CTT ATC AGA
Trp Tyr His Thr Cys Gly Gly Thr Leu Ile Arg
```

FIG.9(a)

```
                        40
CAG AAC TGG GTG ATG ACA GCT GCT CAC TGC GTG
Gln Asn Trp Val Met Thr Ala Ala His Cys Val

GAT TA gtaagaaaaacaaagac ....      ....gggatt
Asp Ty

50            Exon 4
ccttctctcacgccag C CAG AAG ACT TTC CGC GTG
                 r Gln Lys Thr Phe Arg Val 60
GTG GCT GGA GAC CAT AAC CTG AGC CAG AAT GAT
Val Ala Gly Asp His Asn Leu Ser Gln Asn Asp 70
GGC ACT GAG CAG TAC GTG AGT GTG CAG AAG ATC
Gly Thr Glu Gln Tyr Val Ser Val Gln Lys Ile 80
GTG GTG CAT CCA TAC TGG AAC AGC GAT AAC GTG
Val Val His Pro Tyr Trp Asn Ser Asp Asn Val
```

FIG.9(b)

```
                    90
GCT GCC GG gtaggagcaagtcca ....  ... gagcag
Ala Ala Gl Exon 5
tctcctttctcctgcag  C TAT GAC ATC GCC CTG CTG
                   y Tyr Asp Ile Ala Leu Leu 100
CGC CTG GCC CAG AGC GTT ACC CTC AAT AGC TAT
Arg Leu Ala Gln Ser Val Thr Leu Asn Ser Tyr 110
GTC CAG CTG GGT GTT CTG CCC CAG GAG GGA GCC
Val Gln Leu Gly Val Leu Pro Gln Glu Gly Ala 120                                      130
ATC CTG GCT AAC AAC AGT CCC TGC TAC ATC ACA
Ile Leu Ala Asn Asn Ser Pro Cys Tyr Ile Thr GGC TGG GGC AAG ACC AAG A   gtaagttgcctacattgg
Gly Trp Gly Lys Thr Lys T cacaa ....   .... tgtgtcctgttcag  CC AAT GGG
                                  hr Asn Gly
```

FIG. 9(c)

```
              140           Exon 6                  150
            CAG CTG GCC CAG ACC CTG CAG CAG GCT TAC CTG
            Gln Leu Ala Gln Thr Leu Gln Gln Ala Tyr Leu 160
            CCC TCT GTG GAC TAT GCC ATC TGC TCC AGC TCC
            Pro Ser Val Asp Tyr Ala Ile Cys Ser Ser Ser 170
            TCC TAC TGG GGC TCC ACT GTG AAG AAC ACC ATG
            Ser Tyr Trp Gly Ser Thr Val Lys Asn Thr Met 180
            GTG TGT GCT GGT GGA GAT GGA GTT CGC TCT GGA
            Val Cys Ala Gly Gly Asp Gly Val Arg Ser Gly TGT CAG gtgacattgcag ....    .... ctcctccct
            Cys Gln
                              190     Exon  7
            gcag GGT GAC TCT GGG GGC CCC CTC CAT TGC TTG
                 Gly Asp Ser Gly Gly Pro Leu His Cys Leu
```

FIG.9(d)

```
                    200
GTG AAT GGC AAG TAT TCT CTC CAT GGA GTG ACC
Val Asn Gly Lys Tyr Ser Leu His Gly Val Thr

210
AGC TTT GTG TCC AGC CGG GGC TGT AAT GTC TCC
Ser Phe Val Ser Ser Arg Gly Cys Asn Val Ser

220
AGG AAG CCT ACA GTC TTC ACC CGG GTC TCT GCT
Arg Lys Pro Thr Val Phe Thr Arg Val Ser Ala

230
TAC ATC TCC TGG ATA AAT AAT  gtgagtcctctcaaa
Tyr Ile Ser Trp Ile Asn Asn tgatgg ....        ..... tgtctttccttcag GTC
                                         Val Exon 8    240
ATC GCC TCC AAC TGA acatttcc
Ile Ala Ser Asn  -
```

FIG. 9(e)

HUMAN PANCREATIC ELASTASE I

BACKGROUND OF THE INVENTION

This invention relates to human pancreatic elastase. More particularly, but not exclusively, this invention relates to human pancreatic elastase I, to DNA containing a base sequence coding for this elastase, to a host transformed by this DNA and to a process for preparing the elastase using the host Elastase is a serine protease, capable of hydrolyzing the fibrous insoluble protein known as elastin. Elastin is a scleroprotein forming connective tissues, tendons aortic integuments and cervical bundles of higher animals. Elastin is only slightly degraded by other proteases such as pepsin and trypsin.

In the course of their study on arteriosclerosis, Balo' et al observed degradation of the elastin fibers of arterial walls, and postulated the presence of a degrading enzyme (Schweiz Z Pathol Bacteriol, 12, 350 (1949)). Subsequently, in 1952, Banga discovered an enzyme in the pancreas which specifically hydrolyses elastin. The enzyme was isolated in the form of crystals and named "elastase" (Acta Physiol Acad Sci Hung, 3, 317 (1952)).

Elastase has been confirmed to exist in the pancreas of most mammals, including humans, monkeys, cats, rabbits, etc. A correlation is recognized between elastase activity and the age of a human being: a marked lowering in elastase activity in the pancreas and plasma of males over 40 and of females over 60 years has been reported by Loeven and Baldwin (Gerontologia, 17, 170 (1971)).

In the case of patients with arteriosclerosis, the elastase activity in the pancreas was reported by Balo' and Banga to be markedly lower than that of healthy people, and in some cases it had completely disappeared (Nature, 178, 310 (1956)). Subsequent studies have also demonstrated that elastase not only catalyses the hydrolysis of elastin but also accelerates elastin biosynthesis.

Studies on the pharmacological action of elastase have been carried out in rats and rabbits, and have revealed the following effects:

(1) inhibition of the deposition of lipids and calcium on arterial walls;

(2) removal of cholesterol and calcium from arterial walls;

(3) selective degradation of denatured elastin;

(4) acceleration of synthesis of elastin fibers in the arterial walls;

(5) lowering of serum lipids; and (6) improvement of lipoprotein metabolism.

In clinical studies conducted on the basis of the findings mentioned above, the following effects have become apparent after oral administration of elastase:

(1) restoration of elasticity and expandability of arterial walls;

(2) reduction of serum lipid abnormality;

(3) improvement of serum lipoprotein metabolism.

Elastase extracted and purified from porcine pancreas was used for the above studies. Two type of elastase ("elastase I" and "elastase II") exist in the porcine pancreas (Front Matrix Biol, 6, 1 (1978)). The elastase used in the studies was a mixture of elastase I and elastase II, with the former as the main component.

With the administration of porcine elastase to human beings, there is the risk of antibody formation due to the antigenic effect of the foreign protein. There is then the danger of anaphylaxis with repeated administration. Accordingly, human elastase is preferable for human use. However, it is extremely difficult to procure human elastase in sufficient quantities from the traditional source, the human pancreas.

At present, four kinds of human pancreatic elastase are known, human elastases IIA and IIB and human elastases IIIA and IIIB. It has been established that an elastase corresponding to porcine elastase I is little expressed in the human pancreas.

In general, in order to produce a desired protein by use of recombinant DNA technology and a host such as *E. coli*, the complementary DNA (cDNA) of the mRNA of the desired protein is synthesized and then transferred into the host. However, the mRNA for human elastase I is so little expressed in human pancrea that the corresponding cDNA is difficult to obtain.

OBJECTS OF THE PRESENT INVENTION

It is an object of this invention to provide human pancreatic elastase I and make it readily available, with the possibility of obtaining the elastase in substantially pure form. It is further object of this invention to eliminate the continuing dependency on human pancreas for adequate supplies of human pancreatic elastase. It is a yet further object to produce new elastase compounds and elastase-like compounds.

SUMMARY OF THE PRESENT INVENTION

This invention embraces the use of cDNA probes, chromosomal genes and synthesized cDNAs in genetic engineering for the production of human pancreatic elastase I. A cDNA is obtained for the corresponding protein freely expressed in an available animal tissue. By using the animal cDNA as a DNA probe, a chromosomal gene of the desired human protein can be isolated from a human gene library. The sequence of the chromosomal gene can be determined, from which the amino acid sequence of the desired protein can be determined. The cDNA in a general sense, or a coding sequence designed and synthesized by chemical means, can be inserted into a suitable host for expression. Correspondingly, human pancreatic elastase I and functionally similar molecules now become readily available for the first time. Indeed, novel elastases have been discovered and are part of this invention.

Thus, through the use of genetic engineering, it is now possible in accordance with the present invention to provide DNA coding for a molecule capable of functioning as a human pancreatic elastase I. Novel human pancreatic elastase I is provided, as well as derivative molecules which function as human pancreatic elastase I. Such molecules, which include molecules arising from silent mutations, fusion proteins and other compounds functionally effective as human pancreatic elastase I, are included. Thus, any substantially similar protein effective as human pancreatic elastase I, including compounds corresponding to human pancreatic elastase I with one or more deleted, replaced or altered amino acids, and compounds corresponding to human pancreatic elastase I with one or more extra amino acids, are also included. More especially, precursor compounds such as proelastases and preproelastases, especially when expressed by a recombinant DNA sequence, as well as elastases obtained by activation of such precursor compounds, represents a human pancreatic elastase of this invention. Further examples of precursor compounds within this invention include fusion proteins comprising the elastase (optionally in the form of a proelastase or preproelastase) and an amino acid sequence derived from another protein. In particular, such fusion proteins can be obtained when the DNA coding for the elastase is inserted into an expression vector downstream of a promoter.

It will be appreciated that a feature of the invention is the ability to synthesize molecules having the capability to act as human pancreatic elastase I. Such ability is principally a function of the active site of the enzyme. Any enzymatic molecule possessing the requisite catalytically available active site will suffice.

PREFERRED EMBODIMENTS OF THIS INVENTION

More specifically, the basis of the present invention is that the human pancreatic elastase I gene existing in the human genome was cloned by using as a DNA probe a porcine elastase I cDNA (prepared from porcine pancreas, Japanese Patent Kokai ("Laid-Open") 207583 (1985), which corresponds to EP157604A published 9 October 1985 and further corresponds to U.S. Ser. No. 716,189 filed Mar. 26, 1985). The human elastase I chromosomal gene had introns and could not be expressed when transferred in its original form into a host such as E. coli. Its structure, with 7 introns, was examined in detail in order to clarify the amino acid sequence of the human elastase I, and a human elastase I gene without introns was synthesized by chemical means. This gene was then transferred into a host for expression. Thus, the invention permits the desired human elastase I to be obtained in large amounts.

In particular, the present invention further provides a DNA sequence with or without introns and containing a base sequence that codes for human pancreatic elastase I, a process for preparing this DNA and a process for producing human pancreatic elastase I by culturing a host transformed by this DNA.

More particularly, the present invention provides human pancreatic elastase I having an amino acid sequence represented by the general formula (I) as illustrated in FIG. 6.

In considering the amino acid sequence for the elastase, it is to be borne in mind that the present invention embraces any substantially similar protein effective as a human pancreatic elastase I, including compounds with one or more deleted, replaced, altered or extra amino acids.

For the human pancreatic elastase I itself, the N-terminal is simply a hydrogen atom. Derivatives of human pancreatic elastase I may have an extra N-terminal amino acid sequence such as Met or all or part of (N)-Thr Gln Asp Leu pro Glu Thr Asn Ala Arg-(C).

The invention provides a DNA coding for human pancreatic elastase I. Such a DNA can have a base sequence represented by the following formula (II) as illustrated in FIG. 7:
wherein X represents a stop codon, that is TAA, TGA or TAG. The amino acid sequence of formula (I) can be encoded by a different DNA base sequence to that of formula (II), and such a modified DNA sequence is also part of this invention.

The DNA of this invention may optionally have ATG at its 5'-end, which will then code for an additional Met at the N-terminal end of the amino acid sequence. As another option, the DNA may have at its 5'-end a part or all of the sequence (5')-ACC CAG GAC CTT CCG GAA ACC AAT GCC CGC-(3'), which will then code for an extra sequence at the N-terminal end of the amino acid sequence comprising a part or all of (N)-Thr Gln Asp Leu Pro Glu Thr Asn Ala Arg-(C).

PROCESSES OF THIS INVENTION

The DNA of this invention, including the base sequences represented by the formula (II), with optional extensions, can be produced for example, in accordance with the steps (a) to (e). It can be also prepared by steps (a), (b), (c), and (f):

(a) isolation of DNA from human tissue;

(b) construction of a gene library by use of the isolated DNA;

(c) from the gene library, isolation of a chromosomal gene which codes for human elastase I using as a probe a cDNA of an elastase I from another animal;

(d) analysis of the genetic sequence and determination of the amino acid sequence of the human elastase I; and (e) chemical synthesis of DNA capable of coding for the amino acid sequence; or (f) instead of (d) and (e), synthesis of a cDNA on the basis of the mRNA which can be obtained by transferring of the chromosomal gene obtained in (c) into suitable animal cells.

From the DNA, the corresponding protein can then be prepared, for example by the steps of:

(1) inserting the DNA into an expression vector;

(2) introducing the recombinant DNA in to a host organism;

(3) culturing the host under conditions resulting in expression of the DNA sequence; and (4) isolating a compound including the protein.

Considering the process in some more detail, for extraction of the DNA for human tissues, the method of Gross-Bellard et al. appears most suitable because of the low degradation of DNA (Eur J Biochem 36, 32 (1973)). For construction of the gene library, the method of Frischauf using the EMBL vector appears the most suitable (J Mol Biol. 170, 827 (1983)). For selection of clones containing a human elastase I gene from the gene library, the plaque hybridization method (Science, 196, 180 (1977)) appears the most suitable. For the probe, a porcine elastase I cDNA (Japanese Patent Kokai 207583 (1985)) labelled with $^{32}P$ is preferred.

Sequencing of the gene in the selected clone may be by any suitable method. The dideoxy sequence method (Proc Natl Acad Sci USA, 74, 5463 (1977)) is preferred, and the Maxam-Gilbert method (Proc Natl Acad Sci USA, 74, 560 (1977)) is also applicable. Such sequencing gives the base sequence to a human elastase I chromosomal gene with introns.

From the base sequence of the human elastase I chromosomal gene, the amino acid sequence of human elastase I is readily established. A human elastase I gene without introns can then be synthesized. Such synthesis can be achieved for example by the solid phase/phosphoamidite method, for instance by using the DNA synthesizer Model 380B of Applied Biosystems Co.

The synthesized human elastase I gene can be expressed by ligation with a suitable expression vector followed by introduction in to a suitable host. Representative examples of suitable hosts include not only bacteria such as E. coli and B. subtilis and microorganisms such as yeast, but also animal cells.

Preferred promoters for expression in E. coli include tryptophan (trp) promoter, lactose (lac) promoter, tryptophan/lactose (tac) promoter, outer membrane principal protein (Lpp) promoter, λ-PL promoter of bacteriophage origin and protein chain elongating factor Tu (tufB) promoter.

The DNA of the present invention may be introduced into the host using any of several methods, including the Hanahan method (J Mol Biol, 166, 557 (1983)), the calcium chloride method (Gene, 6, 23 (1979)), the low pH method (page 49 of the Manual of Genetic Manipulation, edited by Yasuyuki Takagi, Kodansha Scientific (1982)), etc. The Hanahan method is currently preferred.

The host thus obtained (the recombinant host) can be cultured in a suitable medium to produce and accumulate the human elastase I or a substance having the same effect, followed by recovery thereof.

Typical media for culturing the transformed host include those comprising glucose, casamino acids, and other known components, for example, M9 medium (Experiments in Molecular Genetics, 431 to 433, Cold Spring Harbor Lab, New York (1972)).

The transformed host is generally cultured at 15 to 43° C. for 3 to 24 hours, with aeration or stirring, if necessary. However, when mammalian cells are used as the host, it is usually necessary to carry out the culture for 3 to 10 days.

After culturing, the transformed host can be harvested in a conventional manner, for example by centrifugation or other known techniques. When *B. subtilis*, yeast or mammalians cells are employed as the host, the elastase produced is generally secreted from the cell to the culture broth. However, when *E. coli* is employed as the host, the elastase is mainly present as an undissolved protein in inclusion bodies within the cells. In cases in which *E. coli* is used as the host, the elastase may be obtained by disruption of the cells. For example, the elastase can be obtained as a precipitate after suspending the cells in a buffer, rupturing the cells and centrifugation. The cells may be ruptured by conventional procedures, including sonification treatment, lysozyme treatment or freeze-thaw treatment.

Isolation of elastase from the supernatant or the precipitate may be practiced according to the conventional methods known in the art for the purification of proteins.

The typical human elastase I produced by the present invention include proelastases and other elastase derivatives. After any appropriate activation, the elastases generally exhibit comparable biological activity to those purified from human pancreatic fluid. They can be used for the same purposes and in the same ways as the extracted elastases. Thus, the present invention further provides pharmaceutical compositions which comprise an elastase of this invention, together with a pharmaceutically acceptable carrier or diluent.

Examples of the present Invention

The present invention is illustrated by, the following non-limiting Examples, in which reference is made to the accompanying drawings.

SUMMARY OF THE DRAWINGS

FIG. 6 is the amino acid sequence of general formula (I) for human pancreatic elastase I according to the present invention.

FIG. 7 is the DNA base sequence of general formula (II) for DNA coding for human pancreatic elastase I according to the present invention.

FIG. 8 shows the base sequence of a modified human elastase gene containing added restriction sites to facilitate synthesis of the inventive human elastase I gene.

FIG. 9 which is represented as FIGS. 9(a)–9(e) shows the results of sequence determination within the exon regions of the inventive human elastase I chromosomal gene.

EXAMPLE 1

DNA coding for elastase (1) Preparation of human gene library

Starting from 8.9 g of human pancreas (anatomical specimen). DNA was extracted according to the method of Gross-Bellard et al. (Eur J Biochem. 36, 32 (1973)) to give 2.7 mg of high molecular weight DNA. 84 mcg of the DNA was partially digested with the restriction enzyme Sau3A1 and the partially digested DNA was fractionated by electrophoresis using 0.4% agarose gel to give DNA fragments from 15 Kb to 20 Kb. Using T4 DNA ligase, the DNA fragments obtained in this way were ligated to the vector EMBL4 (Seikagaku Kogyo Co.) digested with Bam H1.

In a similar manner, DNA fragments prepared by partial digestion with Hae3 were connected to the known vector Charon 4A.

After completion of the ligation, in vitro packaging was effected to give two kinds of human gene libraries. For the in vitro packaging, a commercially available in vitro packaging kit from Seikagaku-Kogyo Co was used.

(2) Isolation of human elastase I chromosomal gene

The next step was to isolate a phase clone containing the elastase I gene from the human gene library which had been prepared from the DNA fragments partially digested with Sau3A1 or Hae3. Phage screening was carried out according to the method of Benton and Davis (Science 196, 180 (1977)). Porcine elastase I cDNA (see Japanese Patent Kokai 207583 (1985)) labelled with $^{32}P$ according to the nick-translation method was employed as a DNA probe.

After screening of $4 \times 10^5$ clones for each of the two gene libraries, each library gave a single phage clone which hybridized with the probe. The particular clone isolated from the human gene library of the DNA fragments partially digested with Hae 3 was named φH44-3, and that for Sau 3A1 was named φEL1-16.

From these two phage clones, the DNA was extracted according to the method of "Molecular Cloning" (Molecular Cloning, T. Maniatis et al. Ed., Cold Spring Harbor Laboratory (1982)), giving the respective restriction enzyme maps of FIG. 1A and 1B.

Figure 1:
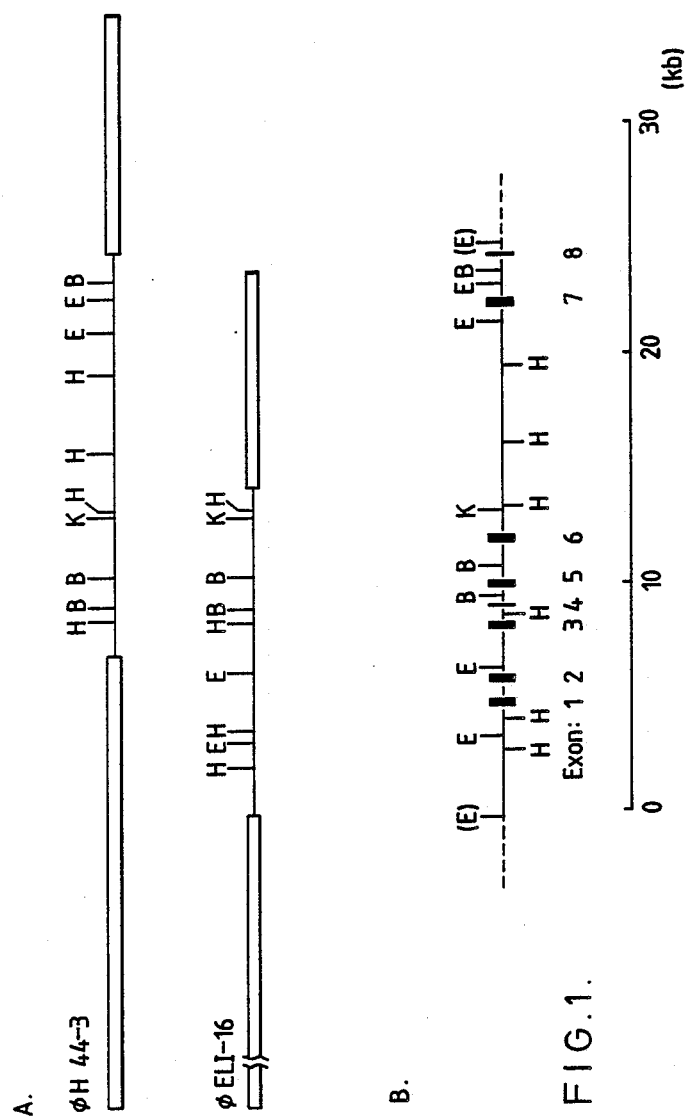
FIG. 1A–B shows restriction endonuclease maps for human elastase I chromosomal genes.

FIG. 1A shows the map when cleaved with φH44-3 and φEL1-16, where the broad lines and the fine lines respectively indicate the vector regions and the inserted human DNA regions. FIG. 1B shows the map determined with φH44-3 and φEL1-16, where the broad solid lines and the fine lines respectively indicate the exon regions and intron regions. In both FIGS. 1A and 1B, the abbreViations E, H, B and K indicate EcoRl. Hind 3, BamHl and KPnl, respectively.

In this way, it was found that the φH44-3 and φEL1-16 had inserts of human genome DNA of 17.3 Kb and 14.5 Kb, respectively. By comparison of the restriction enzyme maps, it was apparent that the human genome DNA inserted in these phage clones had an overlapping sequence of about 7 Kb.

(3) Structure Analysis of Human Elastase I Chromosomal Gene

In order to elucidate the primary structure of the exon regions of the presumed human elastase I chromosomal gene, Southern blotting (J Mol Biol, 98, 503 (1975)) was carried out using as a DNA probe a porcine elastase I cDNA (Japanese Patent Kokai 207583 (1985)). By this blotting, the various exon regions were determined. The base sequence within each of these regions was determined according to the dideoxy sequence method of Sanger, F. et al. (Proc Natl Acad Sci USA, 74, 5463 (1977)).

By comparison of the base sequence thus determined with that of porcine elastase I cDNA and with that of rat elastase I chromosomal gene reported by Swift et al. (J Biol Chem 259, 14271 (1984)). the base sequences within the exon regions of the human elastase I chromosomal gene were determined. For the junction sites of the exons and introns, the base sequences were determined on the basis that there always exists a sequence GT at the 5'-terminal of the intron and a sequence AG at the 3'-terminal of the intron (the GT-AG rule).

The FIG. 9 which is the combined FIGS. 9(a)–9(e) shows the results of these sequence determinations, where the capital letters and the small letters respectively indicate the sequences of the exons and introns, respectively.

The points where the exons joined the introns, and thus the points where the splicing occurs, were identical for the human elastase I chromosomal gene and the rat elastase I chromosomal gene.

It was established that the human elastase I contained 240 amino acids, as does porcine elastase I. The amino acid sequences of human elastase I, porcine elastase I and rat elastase I exhibited sequential similarity with one another at a figure as high as about 90%.

(4) Chemical Synthesis of Human Elastase I Gene

The human elastase I chromosomal gene contained intron regions, and thus it was not possible to produce human elastase I in *E. coli* and *B. subtilis* when the intact gene was introduced in to such bacterial cells. For expression in *E. coli* and other bacteria, a cDNA is generally prepared from mature mRNA, without introns. By Northern blotting (Thomas, P. S. : Proc Natl Acad Sci USA 77, 5201 (1980)) using porcine elastase I cDNA as a DNA probe, it was established that the mRNA of elastase I is transcribed at low levels in the human pancreas. This presented difficulties in synthesizing human elastase I cDNA from mRNA by usual methods.

In order to obtain a gene which might be expressed in *E. coli*, a gene without introns was designed so as to code for human elastase I on the basis of the exon sequences of the human elastase I chromosomal gene, as established by the structural analysis.

In designing the modified human elastase I gene, several restriction sites were added, in order to assist insertion in expression plasmids and for ease of subcloning of the plasmid during synthesis. To this end, 7 bases differing from those of the natural gene were used, within the degeneracy of the genetic code.

The table of FIG. 8 shows the base sequence.

Figure 2:
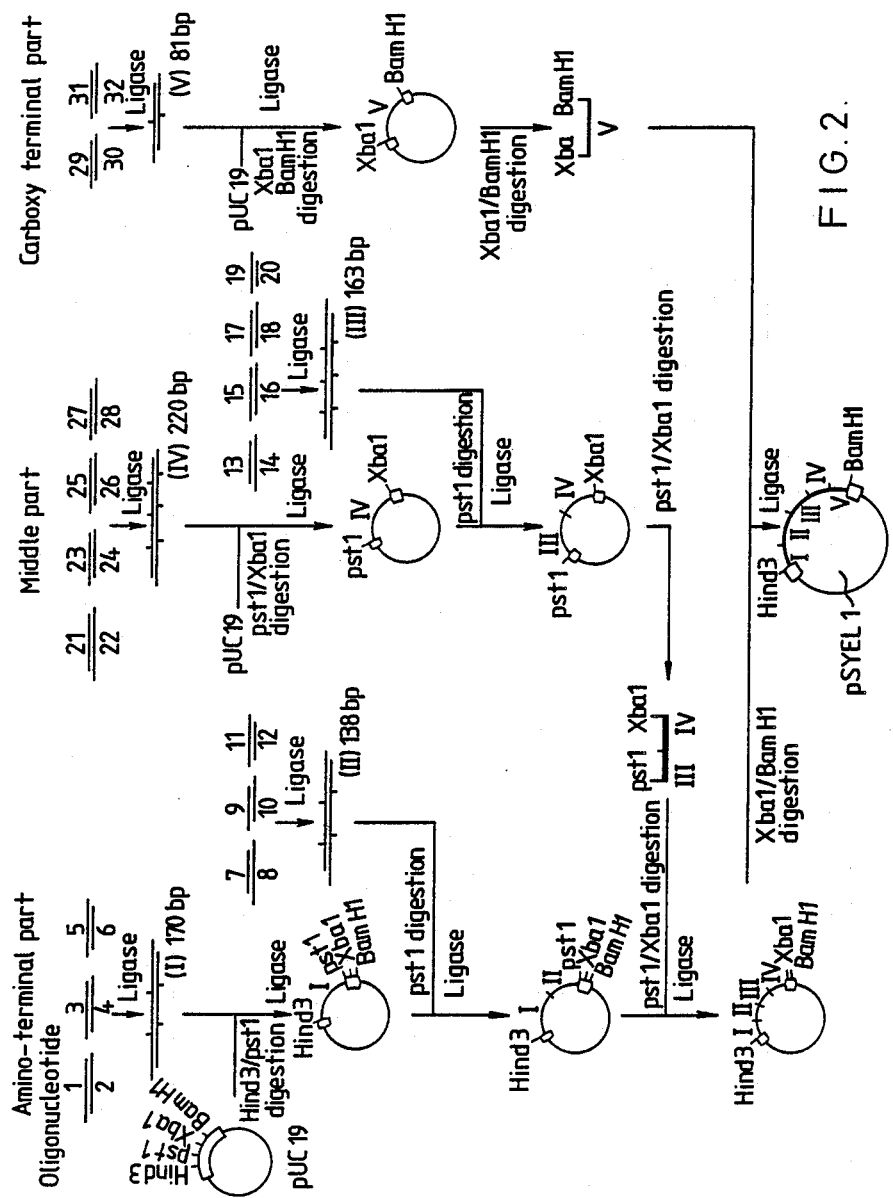
FIG. 2 shows the procedures for constructing a plasmid pSYEL1 in Example 1.

The total synthesis of the gene was achieved by enzymatic ligation in the appropriate sequence of 32 oligonucleotides of from 30 to 57 bases. In practice, three parts of the gene, namely the amino-terminal section, middle section and carboxy-terminal section, were synthesized independently, and after confirmation of the desired base sequence of each section by sequence determination, the three sections were ligated to make a human elastase I gene, as illustrated in FIG. 2.

The chemical synthesis of the oligonucleotides was carried out suing a Model 380 B DNA synthesizer (Applied Biosystems Co), and the resulting oligonucleotides were purified by electrophoresis using 10 to 15% polyacrylamide gel containing urea. Annealing and oligonucleotide ligation reactions with T4 DNA ligase were performed according to the method of Ikehara et al. (Proc Natl Acad Sci USA 81, 5956 (1984)).

The amino-terminal section was synthesized as follows: oligonucleotides 1 to 6' shown in the above table were, after annealing, ligated using T4 DNA ligase. The resulting DNA fragment of 170 base pairs was inserted into known plasmid pUC19 which had been digested with Hind3 and Pst1. The sequence of the synthesized oligonucleotide was confirmed by the dideoxy method. Subsequently, into the Pst1-digested site of the resultant plasmid, a DNA fragment was inserted of 138 base pairs which had been prepared from oligonucleotides 7 to 12. The 5'-terminal base at the N-terminal end of the DNA fragment of 138 base pairs is C, so that Pst1 can not digest this site after insertion. The correct orientation of the inserted DNA was confirmed by determination of the sequence.

The middle section was synthesized as follows: oligonucleotides 21 to 28 after annealing were ligated to form a DNA fragment of 220 base pairs which was then inserted into plasmid pUC19 previously digested with Pst1 and with Xba1, and then the base sequence was confirmed by the dideoxy method. Into the Pst1-digested site of this plasmid, A DNA fragment was inserted of 163 base pairs which had been prepared from oligonucleotides 13 to 20. The 3'- terminal bases at the C-terminal end of the DNA of 163 base pairs is TTGCA, so that Pst1 can not digest this site after insertion.

The carboxy-terminal section was synthesized as follows: oligonucleotides 29 to 32 were, after annealing, ligated with T4 ligase. The resulting DNA fragment of 81 base pairs was inserted into plasmid pUC19 which had been digested with Xba1 and BamH1, and then the base sequence was confirmed by the dideoxy method.

As shown in FIG. 2, the DNA fragment for the middle section was excised using Pst1 and Xba1, and was inserted into the plasmid containing the amino-terminal section, after digestion with Pst1 and with Xba1. In addition, into the Xba1/Bamh1-digested site of this plasmid, the DNA fragment for the carboxy-terminal section excised from the relevant plasmid using Xba1 and BamH1 was inserted in order to obtain a plasmid pSYEL1 which contained the 772 base pairs of the human elastase I gene.

Digestion of plasmid pSYEL1 with Scal and with BamH1 yields DNA coding for proelastase I, and digestion with Sma1 and with BamH1 affords DNA coding for mature elastase I.

The synthesized human elastase I gene can be expressed by insertion into a suitable expression vector followed by introduction into a host, which can bring about production of human elastase I in large amounts.

EXAMPLE 2

Expression in animal cells (1) Construction of expression plasmid pSV2-HEL1

Figure 3:
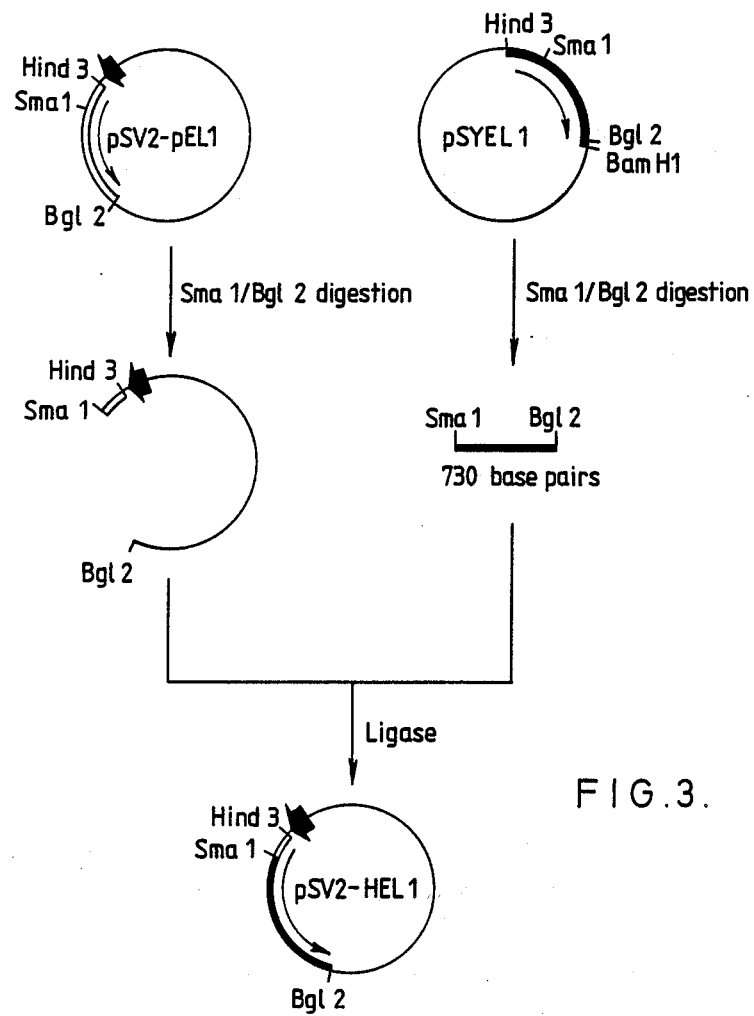
FIG. 3 shows the procedure for constructing plasmid pSV2-HEL1 in Example 2.

In order to achieve expression in host animal cells, the synthesized human elastase I gene was inserted in an expression vector according to the procedures shown in FIG. 3. The known plasmid pSV2 containing the SV40 promoter, enhancer, poly(A) signal and the intron of the small T antigen gene, was used for the expression vector.

Thus, the known plasmid pSV2-PEL1 with inserted porcine elastase I cDNA was digested with the restriction enzymes Sma1 and Bgl2, and a DNA fragment containing the promoter was separated by electrophoresis using agarose gel. The enzymatic reactions can be carried out according as described in "Molecular Cloning" (Maniatis, T. et al. (ed): Molecular Cloning (1982), Cold Spring Harbor Lab.). The broad and fine arrows respectively indicate the promoters from SV40 and the transcription direction of elastase. As further shown in the FIG. 3, the plasmid pSYEL1 of Example 1 was digested with Sma1 and with Bgl2 to obtain a DNA fragment of 730 base pairs which codes for the mature elastase part of the synthesized human elastase I gene. This DNA fragment and the isolated pSV2 fragment containing the promoter were ligated with ligase. In this way, a plasmid PSV2-HEL1 was constructed in which the PSV2 vector and the elastase gene were ligated in the correct orientation for transcription.

(2) Transfection of COS1 cells with the expression plasmid pSV2-HEL1

Transfection of plasmid PSV2-HEL1 into COS1 animal cells was carried out according to the calcium phosphate method of Graham and Van Der Eb (Virology, 52, 456 (1973)). The COS1 cells were seeded at a density of $1 \times 10^6$ cells per dish of 10 cm diameter, and incubated overnight on Dulbecco's modified Eagle medium containing 10% bovine fetal serum. 300 mcg of plasmid PSV2-HEL1 was suspended in 12.55 ml of sterile distilled water, 0.75 ml of 2.5 M $CaCl_2$ solution was added and mixed well. While bubbles were passed through the solution by pipette. 1.5 ml of 10-fold HeBS solution (210 mM of HEPES buffer solution, 1.37 M of NaCl, 4.7 mM of KCl, 10.6 mM of $Na_2HPO_4$, 55.5 mM of glucose; PH 7.05) was dropped in the solution in order to form a precipitate of DNA with calcium phosphate. The precipitate was allowed to mature by standing for 30 minutes at room temperature, and 1 ml of the precipitate was added to each prepared dish of COS1 cells on a fresh medium containing 10% bovine fetal serum. After incubation for 12 hours at 37° C. in the presence of 5% $CO_2$, the culture medium was discarded and replaced with fresh Dulbecco's modified Eagle medium not containing bovine fetal serum. Incubation was continued for an additional 48 hours.

(3) Confirmation of expression by Northern blot hybridization

In order to confirm the existence of human elastase I mRNA transcribed from the expression plasmid in the transfected COS1 cells, Northern blot hybridization was carried out after extracting the mRNA from the COS1 cells.

Thus, to the COS1 cells after incubation for 48 hours, 1 ml per dish of guanidine thiocyanate solution (4 M guanidine thiocyanate, 1% sarcosyl, 20 mM ethylenediamine tetraacetate, 25 mM sodium citrate (pH 7.0), 100 mM 2-mercaptoethanol, 0.1% Antifoam A) was added to lyse the cells. In order to reduce the molecular weight of the high molecular weight DNA, the solution was passed several times through a 21-gauge injection needle. The solution was then laid on a solution of 5.7 M caesium chloride and 0.1 M ethylenediamine tetraacetate, and centrifuged at 30000 rpm, at 20° C., for 17 hours using a Hitachi RPS 40 Swingrotor. After centrifugation, the precipitated RNA was washed with a small amount of ethanol and dissolved in 300 mcl of distilled water. About 1 mg of total RNA was extracted from about $10^8$ of COS1 cells.

The extracted total RNA was subjected to oligo(dT) cellulose column chromatography according to the method of Aviv and Leder (Proc Natl Acad Sci USA 69, 1408 (1972)). giving several mcg of purified mRNA. Northern blot hybridization was carried out using half the purified mRNA, according to Thomas's method (Proc Natl Acad Sci USA 77, 5201 (1980)). The human elastase I gene fragment of 730 base pairs, labelled with $^{32}P$ by the nick translation method (J Mol Biol 113, 237 (1977)), was used as the DNA probe. After hybridization, an mRNA of 1.8 Kb which hybridized with the probe was detected among the mRNA of COS1 cells transfected with PSV2-HEL1. Transcription of PSV2-HEL1 is terminated by the poly(A) signal contained in the vector, and accordingly an mRNA of 1.8 Kb is expected. The value obtained by the Northern blot hybridization accorded with the expected value, and it was concluded that human elastase I mRNA was expressed using the SV40 promoter.

(4) Elastase activity in the supernatant of the cult medium

Human elastase I gene inserted into the plasmid PSV2 according to the procedure shown in the FIG. 3 contains the regions coding for the signal peptide and propeptide of porcine elastase I, and therefore it is to be expected that the expressed human elastase I will be secreted in the medium in the form of a proelastase I containing a propeptide part of porcine elastase I.

The elastase activity in the culture medium was measured after 48 hours cultivation. This analysis of elastase activity was carried out according to the method of Bieth et al. using a synthetic substrate (Front Matrix Biol. 6, 1 (1978)).

To 1 ml of the supernatant of the medium, 200 mcl of 1 M Tris-HC1 buffer solution (PH 8.5) and 50 mcl of trypsin solution containing 10 mg per ml were added. The mixed solution was kept at 25° C. for 15 minutes to activate the proelastase, and then 50 mcl of a soybean trypsin inhibitor solution (10 mg per ml) was added to inactivate the added trypsin. The reaction mixture was then admixed with 10.4 mcl of N-methylpyrrolidone in which had been dissolved 125 mM of succinyl-L-alanyl-L-alanyl-L-alanine-p-nitroanilide (Suc-Ala-Ala-Ala-PNA). After 1 hour of incubation at 25° C., the absorbance at 410 nm was determined.

No elastase activity was detected in the culture medium of only COS1 cells, but, elastase activity was observed in the culture medium where COS1 cells were transfected with pSV2-HEL1.

α-1-antitrypsin or elastatinal, a specific elastase inhibitor, was added to the culture medium showing elastase activity, whether the activity was inhibited or not. By addition of elastatinal or α-1-antitrypsin to the sample solution activated with trypsin, the ability to hydrolyze the synthetic substrate was strongly inhibited. This finding shows that the expressed human elastase I is similar to natural porcine elastase I in the mode of inhibition. In addition, the fact that secreted elastase is activated by trypsin treatment suggests that it is largely in the form of a proelastase.

Though the production of human elastase I in this instance is of short duration (transient expression) because the plasmid pSV2-HEL1 is transfected into COS1 cells, it may be possible to obtain cell lines capable of extended production of human elastase I if a suitable selection marker (for instance, neo gene, dihydrofolate reductase gene or the like) is connected to PSV2-HEL1 and then introduced in to CHO cells, etc.

EXAMPLE 3

Expression in Bacillus subtilis (1) Construction of expression plasmid pHEL001

Figure 4:
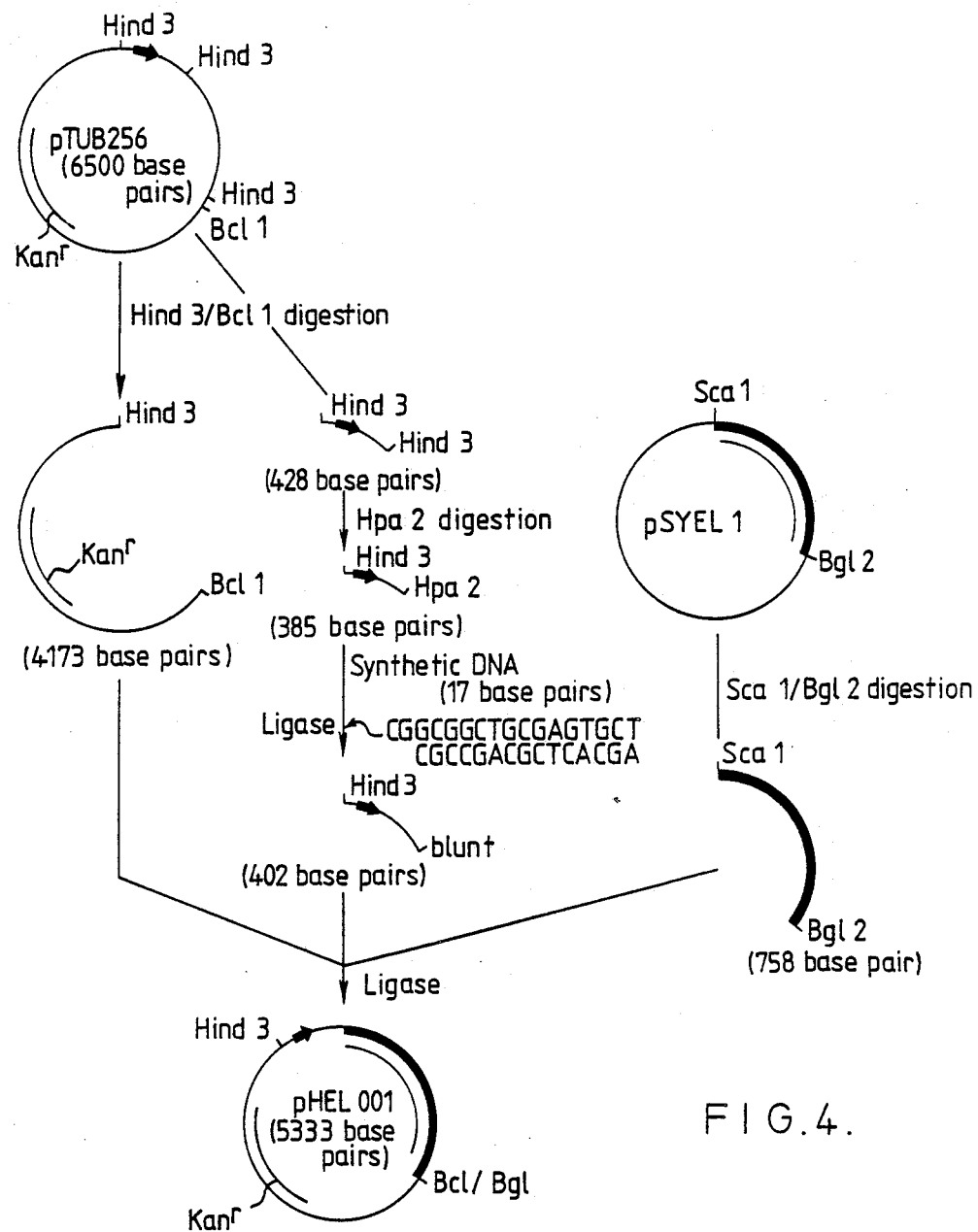
FIG. 4 shows the procedure for constructing plasmid pHEL001 in Example 3.

As shown in FIG. 4, in order to construct the exPression vector, the known plasmid pTUB256 of *B. subtilis* containing the promoter and signal peptide for α-amylase was employed. The broad and fine arrows indicate respectively the promoters from α-amylase and the transcription direction of elastase. First, pTUB256 was digested with restriction enzymes Hind 3 and Bc11, and a DNA fragment of 428 base pairs containing the promoter and a part of the signal sequence for α-amylase, and a DNA fragment of 4173 base pairs containing the origin of replication, were isolated by agarose gel electrophoresis. The DNA fragment of 428 base pairs was further digested with restriction enzyme HPa II and then a DNA fragment of 385 base pairs was obtained after purification by agarose gel electrophoresis. To this DNA fragment, a synthetic DNA which codes for a part of the signal sequence for α-amylase of *B. subtilis* was ligated with T4 ligase.

After agarose gel electrophoresis, a DNA of 402 base pairs was isolated.

Plasmid pSYEL1 was digested with Sca1 and Bgl2 to obtain a DNA fragment of 758 base pairs containing the synthetic human elastase I gene which can code for the mature elastase.

The three DNA fragments were ligated with T4 ligase, and transfected into protoplasts of *B. subtilis*, strain 207–25 (m⁻168 hsrM recE4 AmvE07 aro 1906 leuA48 lvs21; Marburg strain). After regeneration, incubation on a medium containing 10 mcg/ml of kanamycin afforded a transformed strain capable of growing on this medium. By examination of the mode of cleavage with restriction enzymes and by determination of the base sequence, the desired recombinant plasmid PHEL001 was selected from among the plasmids isolated from the transformed strain.

(2) Detection of elastase activity in supernatant of culture medium

*B. subtilis* transformed with the expression plasmid PHEL001 was expected to produce a proelastase containing a propeptide region and secrete it in to the culture medium.

*B. subtilis* strain 207–25 transfected with pHEL001 was incubated with shaking at 35° C. in LG medium (Bacto Tryptone (Difco) 10 g, Bacto yeast extract (Difco) 5 g, NaCl 5 g, glucose 2 g per liter; pH 7.0) containing 50 mcg/ml of kanamycin. To 1 ml of the supernatant of this culture medium were added 200 mcl of 1 M Tris-HCl buffer solution (PH 8.5) and 50 mcl of trypsin solution (10 mg/ml).

After incubating this solution at 25° C. for 15 minutes to activate the proelastase, 50 mcl of soy bean trypsin inhibitor solution (10 mg/ml) was added to inactivate the trypsin. Then, 10.4 mcl of 125 mM Suc-Ala-Ala-Ala-PNA solution was added. The reaction mixture was incubated at 25° C. for 1 hour and the absorbance at 410 nm was determined.

No elastase activity was detected in the culture medium of the control strain 207–25, alone. However, elastase activity was detected in the culture medium of strain 207–25 transfected with PHEL001.

α-1-antitrypsin or elastatinal was added to the culture medium where elastase activity was observed, whether the activity was inhibited or not. When elastatinal or α-1-antitrypsin was added to the sample solution activated with trypsin the hydrolyzing activity for the synthetic substrate was strongly inhibited, as in the case of elastase produced in animal cells. The fact that the enzyme required trypsin treatment for its activation suggested strongly that the produced elastase was in the form of a proelastase.

EXAMPLE 4

Expression in *Escherichia coli*

(1) Construction of expression plasmid pHELO02

Figure 5:
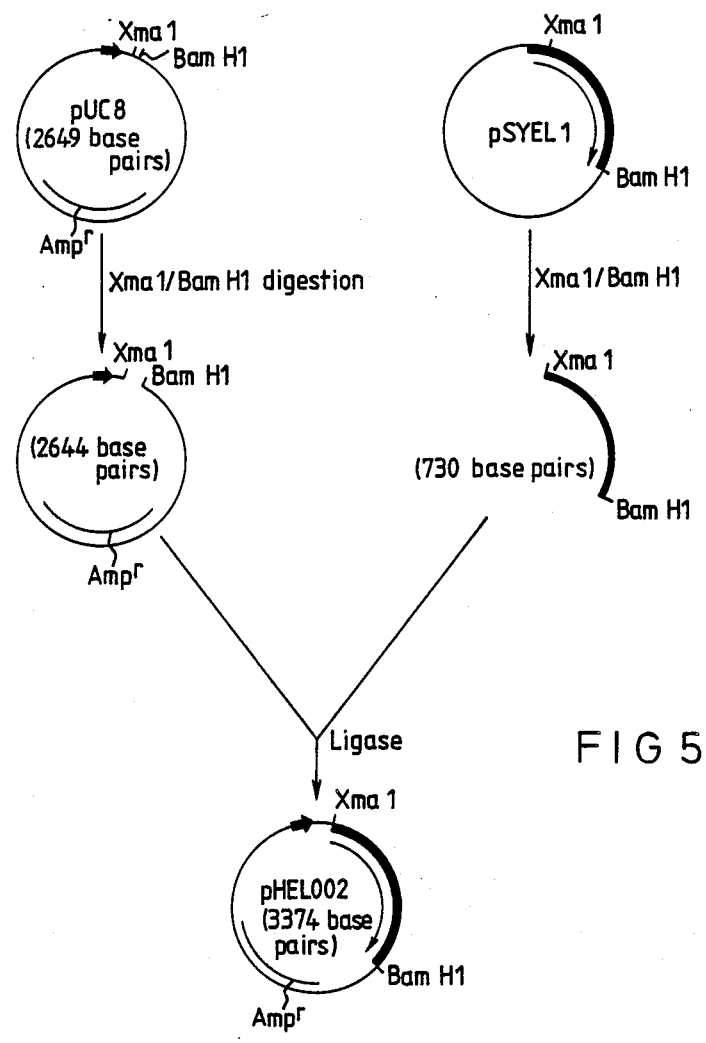
FIG. 5 shows the procedure for constructing plasmid pHEL002 in Example 4.

FIG. 5 shows the procedure which was adopted for constructing the expression vector PHELO02 using *E. coli* as host. As the vector for expression, plasmid PUC8 (Pharmacia Co) containing the lactose promoter was employed. The broad and fine arrows indicate respectively lactose promoters and transcription direction of elastase.

The plasmid PUC8 was digested with XmaI and BamHI and a DNA fragment of 2644 base pairs was obtained by agarose gel electrophoresis. The plasmid PSYEL1 was digested with XbaI and with BamHI to obtain a DNA fragment of 730 base pairs, capable of coding for the mature elastase moiety in the synthetic human elastase I gene.

These two DNA fragments were ligated and employed for transformation of *E. coli* Strain YA21 (F leu met relA) by conventional methods. The desired recombinant plasmid PHELO02 was selected after examination of the cleavage pattern with restriction enzymes and of the DNA base sequence.

(2) Detection of elastase activity in cultured cells.

Strain YA21 transformed with expression plasmid pHEL002 is expected to produce an elastase fusion protein in which 7 amino acids originating from the β-galactosidase of PUC8 were fused to elastase at its N-terminal end.

Strain YA21 transformed with PHELO02 Was incubated at 37° C. for 16 hours in the LB medium. Since the elastase fusion protein existed in the bacterial cells in the form of inclusion bodies, its purification was not complicated.

In detail, from 1 l of the culture medium, 6.5 g of bacterial cells with inclusion bodies was obtained. The bacterial cells were lysed with a 50 mM Tris-HCl buffer solution (pH 8.0) containing 0.2 mg/ml of lysozyme and 1 mg/ml of deoxycholic acid. Unruptured cells were removed by low velocity centrifugation (1500×g, 20 min) and the inclusion bodies were obtained as a pellet by high velocity centrifugation (11000×g, 20 min).

Since the inclusion bodies still contained a large amount of bacterial cell debris, the pellet was re-suspended in a 50 mM Tris-HCl buffer solution containing 5 mg/ml of Triton X-100 and subjected to high velocity centrifugation (11000 ×g, 20 min). The inclusion body pellet was re-suspended in a small amount of Tris-HCl buffer solution and preserved at 4° C.

After these purification steps, 200 mg of inclusion body was obtained which contained about 60% elastase fusion protein (identified by immunoblotting).

As mentioned above, most of the elastase produced by E. coli was found in the inclusion bodies. However, it existed not only in an insoluble fraction of bacterial cells, but also in part in a soluble state, retaining its enzymatic activity intact. Detection of this activity was carried out as follows.

E. coli strain YA21 transformed with elastase I expression plasmid was cultivated in 1 l of the ampicilin medium at 37° C. for 15 hours with shaking. After completion of the cultivation, the bacterial cells were collected by centrifugation at 3000 ×g for 5 minutes, suspended in 20 ml of buffer solution A (50 mM Tris-HCl buffer solution, 1 mM EDTA, 50 mM NaCl; pH 8.0), 10 mg of lysozyme was added, and the mix kept at 5° C. for 20 minutes.

Deoxycholic acid was then added to the suspension to a final concentration of 1 mg/ml, the suspension warmed at 20° C. and deoxyribonuclease added to a final concentration of 0.1 mg/ml. The mixture was then treated in a polytron homogenizer to rupture the bacterial cells. The lysate was centrifuged at 80000 ×g for 40 minutes to remove bacterial cell debris, and subjected to Sephadex G-75 column chromatography. A fraction containing elastase activity was further purified by antibody affinity chromatography to give an elastase I sample for the analysis below.

Elastase activity of the samples was determined as follows. 250 mcl of 100 mM Suc-Ala-Ala-ala-PNA was added to the elastase sample solution, the solution kept warm at 25° for 1 hour and the absorbance at 410 nm was measured. Elastase activity was detected only in the strain YA 21 containing the expression plasmid PHEL002. It was also confirmed at the same time that addition of elastatinal to a final concentration of 0.1 mg/ml inhibited the enzymatic activity.

EXAMPLE 5

Expression in yeast

When yeast was used as a host, in a similar manner to the procedure for animal cells, B. subtilis or E. coli, the DNA of human elastase I was ligated with a suitable expression vector, introduced in to host cells for expression by conventional methods and elastase activity was detected in the culture medium. S. cerevisiae described in "Japanese Guidelines for Recombinant DNA Experiment" was employable for the host, and a strain such as S288C was practically preferable. In addition, ADH1 gene coding for alcohol dehydrogenase gene was preferably employable for the promoter.

We claim:

1. A human pancreatic elastase I having an amino acid sequence of the formula (I) as follows:

(N)-Val Val Gly Gly Thr Glu Ala Gly Arg Asn Ser
Trp Pro Ser Gln Ile Ser Leu Gln Tyr Arg Ser Gly
Gly Ser Trp Tyr His Thr Cys Gly Gly Thr Leu Ile
Arg Gln Asn Trp Val Met Thr Ala Ala His Cys
Val Asp Tyr Gln Lys Thr Phe Arg Val Val Ala
Gly Asp His Asn Leu Ser Gln Asn Asp Gly Thr
Glu Gln Tyr Val Ser Val Gln Lys Ile Val Val His
Pro Tyr Trp Asn Ser Asp Asn Val Ala Ala Gly
Tyr Asp Ile Ala Leu Leu Arg Leu Ala Gln Ser Val
Thr Leu Asn Ser Tyr Val Gln Leu Gly Val Leu
Pro Gln Glu Gly Ala Ile Leu Ala Asn Asn Ser Pro
Cys Tyr Ile Thr Gly Trp Gly Lys Thr Lys Thr
Asn Gly Gln Leu Ala Gln Thr Leu Gln Gln Ala
Tyr Leu Pro Ser Val Asp Tyr Ala Ile Cys Ser Ser
Ser Ser Tyr Trp Gly Ser Thr Val Lys Asn Thr Met
Val Cys Ala Gly Gly Asp Gly Val Arg Ser Gly
Cys Gln Gly Asp Ser Gly Gly Pro Leu His Cys
Leu Val Asn Gly Lys Tyr Ser Leu His Gly Val
Thr Ser Phe Val Ser Ser Arg Gly Cys Asn Val Ser
Arg Lys Pro Thr Val Phe Thr Arg Val Ser Ala
Tyr Ile Ser Trp Ile Asn Asn Val Ile Ala Ser Asn.

wherein (N) represents (1) Met residue (2) Thr Gln Asp Leu Pro Glu Thr Asn Ala Arg or (3) any portion of the peptide of section (2) with the proviso that the C-terminal Arg residue is present.

2. A protein selected from the group consisting of proenzymes, and proproenzymes of the human pancreatic elastase of claim 1.

* * * * *

UNITED STATES PATENT AND TRADEMARK OFFICE
CERTIFICATE OF CORRECTION

PATENT NO. : 4,968,614
DATED : November 6, 1990
INVENTOR(S) : TAKIGUCHI et al

It is certified that error appears in the above-identified patent and that said Letters Patent is hereby corrected as shown below:

Title page, the names of the fourth and fifth inventors should read:

--Toshinori Ohmine; Ichiro Kawashima--.

Column 14, line 46 (claim 2), change:

"proprenzymes" to read --preproenzymes--.

Signed and Sealed this

Eighth Day of June, 1993

Attest:

MICHAEL K. KIRK

Attesting Officer

Acting Commissioner of Patents and Trademarks